United States Patent [19]

Chang et al.

[11] Patent Number: 4,563,476

[45] Date of Patent: Jan. 7, 1986

[54] SUBSTITUTED 5-HYDROXY-2,3-DIHYDROBENZOFURANS AND ANALOGS THEREOF USEFUL AS ANTI-INFLAMMATORY AGENTS

[75] Inventors: Michael N. Chang, Westfield; Milton L. Hammond, Edison; Norman P. Jensen, Princeton; Robert A. Zambias, Hoboken, all of N.J.

[73] Assignee: Merck & Co., Inc., Rahway, N.J.

[21] Appl. No.: 553,668

[22] Filed: Nov. 21, 1983

[51] Int. Cl.[4] .................... A61K 31/34; A61K 31/35; C07D 311/04; C07D 307/79

[52] U.S. Cl. ................................ 514/459; 549/57; 514/253; 549/60; 549/355; 514/309; 549/408; 549/462; 514/310; 549/510; 549/511; 514/312; 514/313; 514/361; 514/362; 514/363; 514/367; 514/369; 514/370; 514/382; 514/383; 514/414; 514/422; 514/443; 514/444; 514/469; 544/405; 546/143; 546/160; 546/269; 548/126; 548/128; 548/151; 548/159; 548/193; 548/256; 548/266; 548/454; 548/525; 549/52

[58] Field of Search ............... 549/408, 462, 355, 510, 549/60, 57; 546/160, 269, 143; 548/256, 454, 525, 126, 128, 193, 159, 151, 266; 544/405, 238; 424/250, 258, 263, 270, 274, 275, 283, 285; 514/253, 309, 310, 312, 313, 361, 362, 363, 383, 414, 422, 443, 444, 459, 469

[56] References Cited

FOREIGN PATENT DOCUMENTS 69521 7/1981 European Pat. Off. .
2617826 4/1975 Fed. Rep. of Germany .
2244458 9/1973 France .

OTHER PUBLICATIONS

Wagner et al., Synthetic Org. Chem., (1953) Wiley & Sons, pp. 660–661.
Aldrich Catalog–Handbook of Org. and Biochemicals, 1975-1976 Ed., Publ. by Aldrich Chem. Co., pp. 738-740.
Handbook of Chem. and Physics, Chem. Rubber Co., 47th Ed. (1966) pp. C-116 through C-121.

Primary Examiner—Richard A. Schwartz
Assistant Examiner—Bernard I. Dentz
Attorney, Agent, or Firm—Theresa Y. Cheng; Mario A. Monaco

[57] ABSTRACT

Substituted 5-hydroxy-2,3-dihydrobenzofuran and analogs such as the substituted 6-hydroxy-2,3-dihydrobenzopyrans were prepared from an appropriately substituted (5-hydroxy-2,3-dihydrobenzofuran-6-yl) formaldehyde or analog thereof with an aryl amine followed by reduction. These compounds were found to be potent topical anti-inflammatory agents.

12 Claims, No Drawings

SUBSTITUTED 5-HYDROXY-2,3-DIHYDROBENZOFURANS AND ANALOGS THEREOF USEFUL AS ANTI-INFLAMMATORY AGENTS

BACKGROUND OF THE INVENTION

The present invention relates to novel substituted 5-hydroxy-2,3-dihydrobenzofurans and analogs thereof useful as anti-inflammatory agents.

It has been observed that the novel compounds of this invention are active in vitro in both the peritoneal macrophage assay and the polymorphonuclear leukocyte assay for general anti-inflammatory activity. Specifically, they are found to be active in vivo in the mouse ear assay for topical anti-inflammatory agents. Furthermore, these compounds tend to be inactivated in vivo after deeper and longer penetration into the body system and are therefore devoid of any significant adverse side effects normally associated with systemic activity.

Recent studies demonstrated that macrophages participate in the development and progression of chronic inflammatory diseases such as rheumatoid arthritis. During the progression of inflammatory conditions, there is generally an appearance and/or presence of macrophages and lymphocytes, especially macrophages and polymorphonuclear leukocytes. Macrophages are known to secrete various products in response to inflammatory stimuli. For example:

(1) Neutral proteases—the destructive peptide bond cleaving enzymes which have been shown to be directly involved in rheumatoid cartilage destruction; and (2) Prostaglandins (PG) (e.g., $E_2$ and $I_2$ by mouse peritoneal macrophages) and other arachidonic acid derivatives derived from both the cyclooxygenase and the lipoxygenase pathways.

These arachidonic acid oxygenation products have been identified as the critical mediators of various acute inflammatory conditions.

Accordingly, pharmacological agents which inhibit the formation or the release of a mediator and thereby interfer with the function of macrophages of polymorphonuclear leukocytes may also be effective anti-inflammatory agents. Generally such a pharmacological agent can be used in the treatment of rheumatoid arthritis, emphysema, bronchial inflammation, osteoarthritis, acute respiratory distress syndrome, spondylitis, lupus, gout, psoriasis and other inflammatory diseases.

Regarding the topical mouse ear assay, it has been previously established that classical nonsteroidal anti-inflammatory agents such as indomethacin and steroidal anti-inflammatory agents such as dexamethasone are active in this assay.

Normally, anti-inflammatory agents which are not significantly systemically active are advantageous because they do not show the kind of adverse effects, e.g., gastrointestinal ulcerations and bleeding that often plagued users of systemic NSAIAs (non-steroidal anti-inflammatory agents). Accordingly, an object of this invention is to provide novel 5-hydroxy-2,3-dihydrobenzofuran derivatives and analogs thereof for the treatment of inflammatory conditions and prusitus such as sunburn, erythema, eczema, contact dermatitis, allergic dermatitis, and psoriasis. It is also intended that these compounds be used for the treatment of peridontal disease and for the treatment of inflammatory bowel disease.

Another object of this invention is to provide appropriate processes for the preparation of the subject novel compounds.

Still a further object of the present invention is to provide a pharmaceutically acceptable composition containing an effective amount of the active compound for the treatment of various inflammatory conditions.

Finally, it is the ultimate object of this invention to develop a method of treating inflammation via the administration of a therapeutically effective amount of the novel compounds or pharmaceutically acceptable composition thereof to a mammalian species in need of such treatment.

DETAILED DESCRIPTION OF THE INVENTION

A. Scope of the Invention

This invention relates to novel compounds of formula (I):

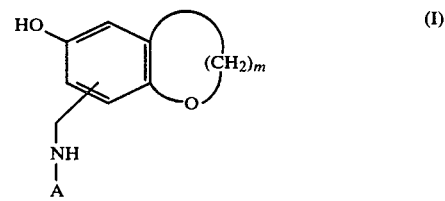

or a pharmaceutically acceptable salt thereof, wherein
  m is an integer ranging from 1 to 4;
  A is (a) phenyl substituted with $(R^1)_q$ wherein when there are more than one $R^1$ (ie, $q>1$), they can be the same or different from each other and is
  (1) hydrogen;
  (2) halo especially fluoro, chloro or bromo;
  (3) loweralkoxy especially $C_{1-6}$ alkoxy, e.g., methoxy, ethoxy, isopropoxy, t-butoxy or cyclohexyloxy, or —OCH$_2$O—;
  (4) lower alkylthio especially $C_{1-6}$ alkythio, or $C_{1-6}$ haloalkylthio e.g., methylthio, ethylthio, trifluoromethylthio or cyclohexylthio;
  (5) lower alkyl sulfinyl especially $C_{1-6}$ alkyl sulfinyl, e.g., methyl sulfinyl, i-propyl sulfinyl, and cyclopentyl sulfinyl;
  (6) lower alkyl sulfonyl especially $C_{1-6}$ alkyl sulfonyl such as methyl sulfonyl, ethyl sulfonyl and n-butyl sulfonyl;
  (7) unsubstituted or substituted phenyl loweralkoxy such as benzyloxy;
  (8) loweralkyl especially $C_{1-6}$ alkyl such as methyl, ethyl, propyl, t-butyl, pentyl, benzyl, cyclopropyl, cyclopentyl or cyclohexyl;
  (9) loweralkenyl especially $C_{2-6}$ alkenyl, for example, vinyl, allyl, and buten-2-yl;
  (10) lower alkanoyl especially $C_{1-6}$alkanoyl such as formyl, acetyl or i-propanoyl;
  (11) haloloweralkyl especially $C_{1-6}$haloalkyl such as trifluoromethyl;
  (12) —COOH or —COOC$_{1-6}$alkyl;
  (13) aryl especially phenyl or substituted phenyl, e.g., 4-methoxyphenyl, 2,4-difluorophenyl or 3-chlorophenyl; or
  (14) aryloxy especially phenoxy;
  (15) cyano;
  (16) hydroxyloweralkyl especially hydroxy $C_{1-3}$alkyl such as —CH$_2$OH;

(17) halo loweralkanoyl especially haloC$_{1-6}$ alkanoyl eq. CF$_3$CO;
(18) heteroaryl as defined below; or
(19) loweralkanoyloxy especially acetyloxy;
q is an integer ranging from 0 to 5;
(b) unsubstituted or substituted heteroaryl, for example:
(1) thienyl;
(2) benzothienyl;
(3) furyl;
(4) benzofuryl;
(5) pyrryl;
(6) indolyl;
(7) thiazolyl;
(8) benzothiazolyl;
(9) thiadiazolyl;
(10) benzothiadiazolyl;
(11) quinolyl;
(12) isoquinolyl;
(13) pyrazinyl;
(14) tetrazolyl; or
(15) triazolyl The heteroaryl above can be substituted with one or more of R$^1$, e.g., C$_{1-6}$ alkyl, C$_{1-6}$alkanoyl, C$_{1-6}$haloalkyl, halo, cyano, or hydroxy C$_{1-3}$alkyl.

In a preferred embodiment of this invention,
A is phenyl substituted with (R$^1$)$_q$ wherein R$^1$ is
(a) hydrogen;
(b) loweralkoxy;
(c) halo;
(d) lowerhaloalkyl,
(e) loweralkanoyl;
(f) hydroxyloweralkyl; or
(g) CN;
q is 1 or 2; and
m is 1 or 2.

In a more preferred embodiment of the present invention, the compounds are of the following formulae:

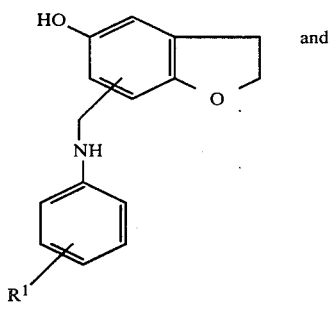

(a)

and

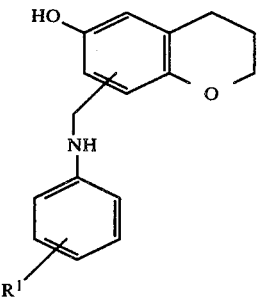

(b)

wherein R$^1$ is loweralkanoyl, hydroxyloweralkyl or halo.

B. Prior Art of the Invention

EPO Pat. No. 69-521 published July 1, 1981 discloses, among other anti-inflammatory agents, pyridinyldihydrobenzofuran derivatives and its imidazolyl analogs of formula:

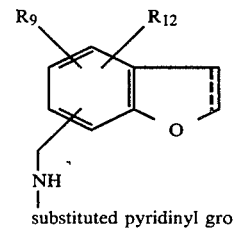

substituted pyridinyl group wherein R$_9$ and R$_{12}$ are H, OH, 1-4C alkyl, halo or CH$_3$O. These compounds are related to but not identical to some of the heteroaryl analogs of the compounds of the present invention.

C. Preparation of the Compounds within the Scope of the Invention:

The novel compounds of the present invention are prepared from the following processes:

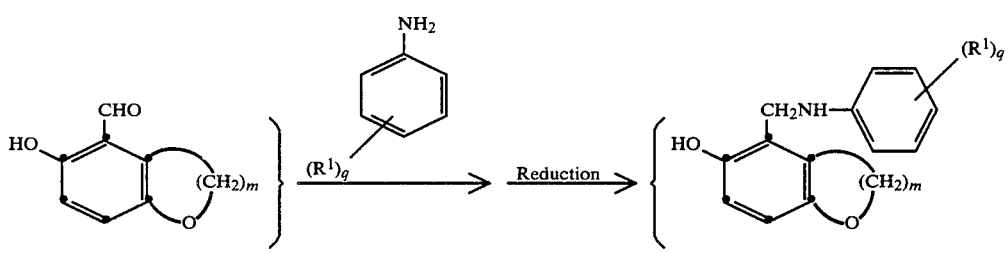

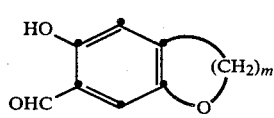

or

Scheme (a) for example:

Step A:

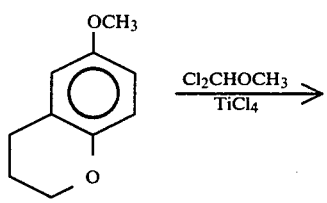

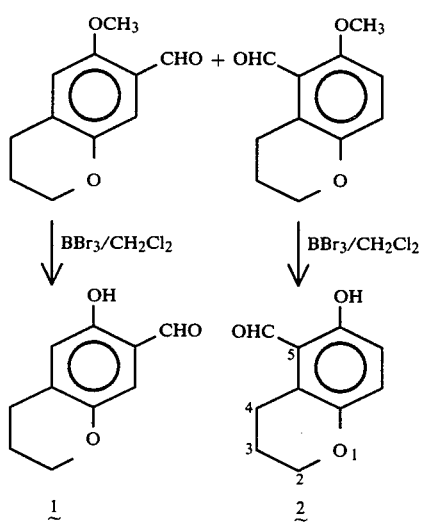

Step B:

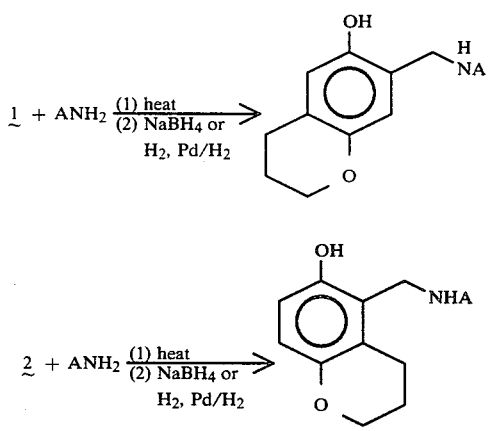

Scheme (b) for example:

Step A:

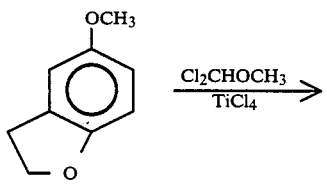

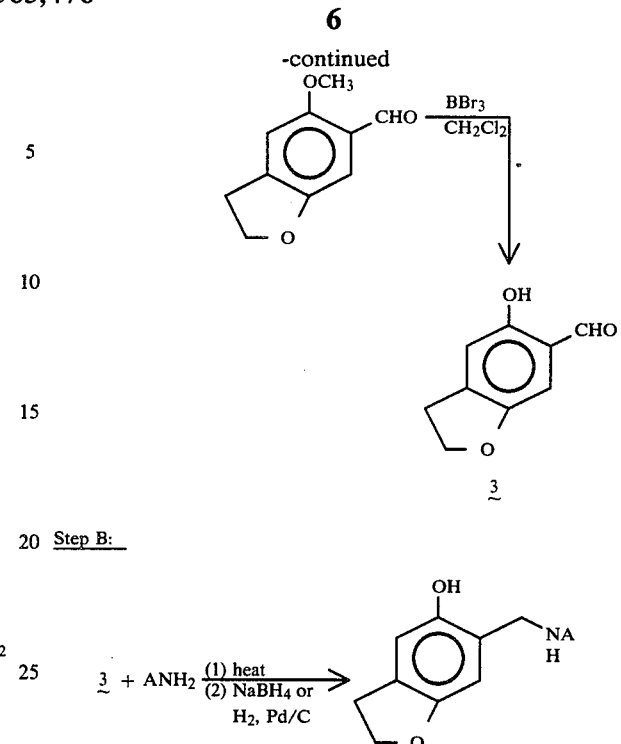

Step B:

C. Utility of the Subject Compounds of the Invention

This invention also relates to a method of treating inflammation in patients in need of such treatment. Generally, a sufficient amount of a compound of formulae (I) or a pharmaceutical composition thereof, particularly an especially preferred compound, is administered to the patient as the active constituent.

For the treatment of inflammation, arthritis conditions, psoriasis, asthma, or other diseases mediated by prostaglandins, a compound of Formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intravascular injection or infusion techniques. In addition to the treatment of warm-blooded animals such as mice, rats, horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Preferably, the compounds of the invention are administered topically, by inhalation spray or rectally in dosage unit formulations containing conventional non-toxic pharmaceutically acceptable carriers, adjuvants and vehicles.

The pharmaceutical compositions containing one or more compounds of formula (I) are suitable for topical use when they are in the form of aqueous or oily solutions or suspensions, dispersible powders or granules, tinctures, topical aerosol emulsions, creams, ointments, jellies, suppositories or the like. These topical compositions may be prepared according to any method known to the art.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. The said aqueous suspensions may also contain one or more preservatives, for example, ethyl, or n-propyl p-hydroxybenzoate.

Oily suspension may be formulated by suspending the active ingredient in a vegetable oil, for example, arachis oil, olive oil, sesame oil or coconut oil, or in a mineral oil such as liquid paraffin. The oily suspensions may contain a thickening agent, for example, beeswax, hard paraffin or cetyl alcohol. These compositions may be preserved by the addition of an antioxidant such as ascorbic acid.

Dispersible powders and granules are suitable for the preparation of an aqueous suspension by mixing them with water. They provide the active ingredient in admixture with a dispersing or wetting agent, a suspending agent and one or more preservatives. Suitable dispersing or wetting agents and suspending agents are exemplified by those already mentioned above.

The pharmaceutical compositions of the invention may also be in the form of oil-in-water emulsions. The oily phase may be a vegetable oil, for example, olive oil or arachis oils, or a mineral oil, for example, liquid paraffin or mixtures of these. Suitable emulsifying agents may be naturally occurring gums, for example, gum acacia or gum tragacanth, naturally-occurring phosphatides, for example, soy bean, lecithin, and esters or partial esters derived from fatty acids and hexitol anhydrides, for example, sorbitan mono-oleate, and condensation products of the said partial esters with ethylene oxide, for example, polyoxyethylene sorbitan monooleate.

An ointment containing the pharmaceutical compositions of the present invention may be prepared, among other methods known in the art, by combining the active ingredient with a medium consisting of a glycol, a lower alkanol, and water; a gelling agent; and optionally an adjuvant such as diisopropyl adipate, diethyl sebacate, ethyl carproate and ethyl laurate. Suitable glycols include propylene glycol, butylene glycol, polyethylene glycol and the like. Generally, a carboxyvinyl polymer preneutralized with an organic amine such as diisopropyl amine and triethylamine, or a cellulose, e.g., hydroxyethyl cellulose, methyl cellulose, carboxymethyl cellulose, hydroxypropyl cellulose, is used as the gelling agent.

The compounds of the invention may also be administered in the form of supporitories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Dosage levels of the order to 0.2 mg to 140 mg per kilogram of body weight per day are useful in the treatment of the above-indicated conditions (10 mg to 7 gms per patient per day). For example, inflammation is effectively treated by the administration from about 0.5 to 50 mg of the compound per kilogram of body weight per day (25 mg to 5 gms per patient per day).

The amount of active ingredient that may be combined with the carrier materials to produce a single dosage form will vary depending upon the host treated and the particular mode of administration. Dosage unit forms will generally contain between from about 25 mg to about 1 g of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

Set forth below are some illustrative topical formulations containing a selected active compound of the instant invention.

Formulation Number 1—Solution (a) Distilled water qs to 100%
Procedure: Dissolve a compound of formula (I) in enough water to make 100%. Filter the solution. Apply to the affected area.

Formulation Number 2—Tincture (b) Alcohol U.S.P.—50%
Water qs to 100%
Procedure: Dissolve a compound of formula (I) in the alcohol. Add sufficient water to make 100%. Filter and apply to affected area.

Formulation Number 3—Topical Aerosol (c) Alcohol U.S.P.—5%
Isopropylmyristate—5%
Conventional halogenated hydrocarbon propellant qs 100% e.g., Freon 11 (trichlorofluoromethane), Freon 12(dichlorodifluoromethane), Freon 14 (carbon tetrafluoride), Freon C 318 (Octafluorobyclobutane), Freon 114 (Cryofluorane), etc.
Procedure: Dissolve a compound of formula (I) in the alcohol and isopropylmyristate. Add sufficient halogenated propellant and introduce into conventional aerosol container either by pressure or by cold filing. Apply to affected area.

Formulation Number 4—Ointment

Petrolatum U.S.P. qs to 100%
Procedure: Heat the petrolatum to 60° C. Add compound (d) and stir until thoroughly dispersed. Cool to room temperature. Apply to affected area.

D. Bioassay in Support of the Utility of the Invention

To establish the utility of the present invention, the novel compounds of Formula I were tested by the following well-known bioassay:

The Topical Mouse Ear Assay

The topical mouse ear assay (TME) is the method by which the novel compounds of the present invention are evaluated for its effect on inflammatory responses elicited by topically applied phorbol myristate acetate (PMA) or topically applied arachidonic acid (AA). The inflammatory responses may be in the form of edema (measured by wet weight); vascular permeability (measured by $^{125}$I-BSA accumulation); or PMN infiltration (measured by myeloperoxidase activity). A protocol of the assay and some results derived therefrom are summarized below.

Protocol for the Topical Mouse Ear Assay

Method: The right ears of mice (5 mice per group) were treated topically with either 5 µl PMA or 1000 µg AA alone or with the test compound in 25 µl of vehicle. The vehicle was water/pyridine/acetone (1:2:97). A control group of mice received the vehicle only. The mice were allowed food and water ad libitum during the treatment period; 2 hours for AA and 4 hours for PMA. The mice were sacrificed by cervical dislocation and a 6 mm diameter disc of tissue punched from both the treated and untreated ears. The tissue biopsies were immediately weighed and the weight increase of the treated ear relative to the weight of the untreated ear determined.

For the determination of vascular permeability, µCi $^{125}$I-bovine serum albumin ($^{125}$I-BSA) was administered in 0.5 ml phosphate buffered saline 15 min prior to the topical application. At the termination of the experiment, the amount of radioactivity in both the treated and untreated ear biopsies was determined and the increased amount of radioactivity in the treated tissue relative to the amount of radioactive in the untreated tissue determined.

As a measure of PMN infiltration, the amount of myeloperoxidase (MPO) activity in the same tissues was determined. The tissue biopsies were homogenized into 1 ml 0.5% hexadecyltrimethylammonium bromide and centrifuged for 45 min. at 1200×g. Aliquots 40 µl, of the supernatant phases were assayed for MPO activity by a colorimetric method devised by H. Dougherty for automated Titertek analysis. The MPO activity is expressed as the $OD_{450}$ of the treated ear homogenate minus the $OD_{450}$ of the non-treated ear homogenate.

All of the data are expressed as the mean ±SEM, N=5 mice/group.

| Results: The effect of 5-hydroxy-6-(4-acetylphenyl-aminomethyl)-2,3-dihydrobenzofuran (A) | | |
|---|---|---|
| Compound | Dosage (µg) | Edema (% inhibition) |
| A | 400 | 76 |
|   | 200 | 60 |
|   | 100 | 45 |
|   | 50 | 44 |
| Indomethacin | 400 | 85 |
|   | 200 | 46 |
|   | 100 | 42 |
|   | 50 | 24 |

EXAMPLE 1

6-Hydroxy-5-(4-acetylphenyl)aminemethyl-3,4-dihydrobenzopyran

Step A: Preparation of
6-methoxy-3,4-dihydrobenzopyran-5-carboxaldehyde-
6-methoxy-3,4-dihydrobenzopyran-7-carboxaldehyde
and
6-methoxy-3,4-dihydrobenzopyran-8-carboxaldehyde A solution of 6-methoxy-3,4-dihydrobenzopyran (133.0 g, 811 mmol) in dry methylene chloride (1850 mL) was cooled to 5° under nitrogen and titanium tetrachloride (145 mL, 250.2 g, 1319 mmol) was added dropwise over 15 minutes. Upon completion of this addition dichloromethylmethylether (60 mL, 76.26 g, 663 mmol) was added dropwise over 45 minutes. A slight exotherm was observed during this addition (reaction temperature—16°). The cooling bath, was removed and the mixture allowed to stir for three hours, then quenched by the dropwise addition of water (300 mL). The resulting mixture was poured into water (1000 mL) the layers separated, and the organic layer washed with water (1000 mL). The combined aqueous layers were back extracted with methylene chloride (500 mL), then the combined organic extracts were washed with brine (2×1000 mL), dried ($Na_2SO_4$) and concentrated to a dark oil (152.0 g). Purification by preparative HPLC (Waters Prep 500, 9:1 hexane:ethyl acetate as eluant) afforded, in order of elution, 6-methoxy-3,4-dihydrobenzopyran-5- carboxaldehyde (32.52 g, 20.9%) m.p. 52°–54° C., 6-methoxy-3,4-dihydrobenzopyran-8-carboxaldehyde (31.83 g, 20.4%) m.p. 69°–71° C., and 6-methoxy-3,4- dihydrobenzopyran-7-carboxaldehyde (31.49 g, 20.2%) m.p. 57°–59° C.

Step B: Preparation of
6-hydroxy-3,4-dihydrobenzopyran-5-carboxaldehyde

A solution of 6-methoxy-3,4-dihydrobenzopyran-5-carboxaldehyde (30.00 g, 156 mmol) in dry methylene chloride (625 mL) was cooled to an internal temperature of −67°. A solution of boron tribromide (1M in methylene chloride, 67.5 mL, 67.5 mmol) was added dropwise. The cooling bath was removed and the mixture allowed to stir under nitrogen for three hours. The reaction was then quenched by the dropwise addition of methanol (75 mL) and the resulting mixture poured into satureated aqueous sodium chloride (1200 mL). The layers were separated and the organic extract washed with saturated sodium chloride (600 mL), dried (Na$_2$SO$_4$) and concentrated. Purification by preparative HPLC (Waters Prep 500, 9:1 hexane: ethyl acetate as eluant) afforded 6-hydroxy-3,4-dihydrobenzopyran-5-carboxaldehyde (22.46 g, 80.8%), m.p. 93–95.

Following substantially the same procedure as described above, but substituting for the 6-methoxy-3,4-dihydro-benzopyran-5-carboxaldehyde, the 6-methoxy-3,4dihydrobenzopyran-7-carboxaldehyde prepared in Step A, there was obtained the corresponding 6-hydroxy-derivatives, i.e., 6-Hydroxy-3,4-dihydrobenzopyran-7-carboxaldehyde (67.6%), m.p. 97°–100° C.

Step C: Preparation of 6-hydroxy-5-(4-acetylphenyl) aminomethyl-3,4-dihydrobenzopyran A mixture of 6-hydroxy-3,4-dihydrobenzopyran-5-carboxaldehyde (308 mg, 1.73 mmol) and p-aminoacetophenone (236 mg, 1.73 mmol) in methanol (8 mL) was heated at reflux for one hour. The mixture was cooled to 15° at which time the intermediate Schiff's base crystallized. After filtration and drying a light orange product (221 mg, 43.3%) was obtained. This material was suspended in methanol (8 mL) and sodium borohydride (28 mg, 0.74 mmol) was added. After stirring at room temperature for ten minutes the mixture was poured into water (75 mL) and the resulting suspension neutralized (pH=7) with 2.5 N HCl. The product was collected by filtration and dried to afford 6-hydroxy-5-(4-acetylphenyl) aminomethyl-3,4-dihydrobenzopyran (170 mg, 76.6%), m.p. 213°–215° C.

EXAMPLE 2

6-Hydroxy-5-(2,4-difluorophenyl)aminomethyl-3,4-dihydrobenzopyran

A mixture of 6-hydroxy-3,4-dihydrobenzopyran-5-carboxaldehyde (299 mg, 1.68 mmol) and 2,4-difluoroaniline (219 mg, 1.68 mmol) in methanol (8 mL) was heated to reflux for 20 minutes during which time the intermediate Schiff's base crystallized, and, after cooling to room temperature, was collected by filtration and dried. The isolated Schiff's base (175 mg, 36%) was suspended in methanol (8 mL) and sodium borohydride (25 mg, 0.66 mmol) was added. The mixture was stirred at room temperature for 5 minutes, poured into water (50 mL) and carefully neutralized (pH=7) with 2.5 N HCl. The product was collected by filtration and dried to afford 6-hydroxy-5-(2,4-difluorophenyl)aminomethyl-3, 4-dihydrobenzopyran, (170 mg, 96.6%), m.p. 120°–121° C.

EXAMPLE 3

6-Hydroxy-5-phenylaminomethyl-3,4-dihydrobenzopyran

A mixture of 6-hydroxy-dihydrobenzopyran- 5-carboxaldehyde (206 mg, 1.16 mmol) and aniline (108 mg, 1.16 mmol) in benzene (6 mL) was heated to reflux for 30 minutes under nitrogen. After cooling the mixture was passed through a short column of silica gel and the eluate concentrated to an orange solid (119 mg). This material was taken up in methanol (10 mL) and hydrogenated at 40 psi using 10% Pd/C (12 mg) as catalyst. After filtration and concentration the crude product was purified by chromatography over silica gel (Hexane/ethyl acetate, 85/15, an eluant) to afford 6-hydroxy-5-phenylaminomethyl-3,4-dihydrobenzopyran (77 mg, 26%) m.p. 105°–107° C.

EXAMPLE 4

6-Hydroxy-5-(2-hydroxymethylphenyl)aminomethyl-3,4-dihydrobenzopyran

A mixture of 6-hydroxy-3,4 -dihydrobenzopyran-5-carboxaldehyde (400 mg, 2.25 mmol) and o-aminobenzylalcohol (282 mg, 2.25 mmol) in methanol (30 mL) was brought to a gentle boil and the volume slowly concentrated to 10 mL. An additional portion of methanol (20 mL) was added and this process was repeated two times. the mixture was cooled (ice bath) at which point the Schiff's base crystallized out and was collected by filtration. This material (450 mg) was redissolved in methanol (30 mL) and sodium borohydride (63 mg, 1.67 mmol) was added in portions. The color was discharged immediately, and the mixture allowed to stir at room temperature for 10 minutes. The reaction mixture was concentrated to half its original volume, then poured into water (35 mL). Acidification with 2 N HCl resulted in complete dissolution of the resulting solid and upon basification with 7% NaHCO$_3$ the product precipitated. The product was collected by filtration and vacuum dried to afford 6-hydroxy-5-(2-hydroxymethylphenyl)aminomethyl-3,4-dihydrobenzopyran (375 mg, 58.5%), m.p. 151°–153° C.

EXAMPLE 5

6-Hydroxy-7-(2,4-difluorophenyl)aminomethyl-3,4-dihydrobenzopyran

A mixture of 6-hydroxy-3,4-dihydrobenzopyran-7-carboxaldehyde (414 mg, 2.33 mmol) and 2,4-difluoroaniline (303 mg, 2.33 mmol) in methanol (8 mL) was heated to reflux. After a few minutes copious amounts of precipitate were deposited. The mixture was cooled to room temperature, and the precipitate collected by filtration and dried to afford the intermediate Schiff's base (455 mg, 68%).

A portion of the Schiff's base (450 mg, 1.97 mmol) was suspended in methanol (20 mL) and sodium borohydride (60 mg, 1.59 mmol) was added in portions. Upon completion of the addition, the mixture was stirred at room temperature for 10 minutes, then poured into water (75 mL). The resulting suspension was neutralized (pH=7) with 2.5 N HCl, and the product collected by filtration. After washing with water and drying 6-hydroxy-7-(2,4-difluorophenyl)aminomethyl-3,4-dihydrobenzopyran (350) mg, 77%) was obtained, m.p. 103°–105° C.

EXAMPLE 6

6-Hydroxy-7-(4-acetylphenyl)aminomethyl-3,4-dihydrobenzopyran

A mixture of 6-hydroxy-3,4-dihydrobenzopyran-7-carboxaldehyde (400 mg, 2.25 mmol) and p-aminoacetophenone (304 mg, 2,25 mmol) in methanol (8.0 mL) was heated to reflux for 20 minutes. Upon cooling, the intermediate Schiff's base, which crystallized, was collected by filtration (525 mg, 795).

The Schiff's base (516 mg, 1.75 mmol) was suspended in methanol (15 mL) and sodium borohydride (66 mg, 1.75 mmol) was added in portions. The mixture was stirred at room temperature for ten minutes then poured into water (100 mL). The mixture was neutralized (pH=7) with 2.5 N HCl and the resulting suspension filtered. The filter cake was washed with 50% aqueous methanol, then dried to afford 6-hydroxy-7-(4-acetylphenyl)aminomethyl-3,4-dihydrobenzopyran (460mg, 88%), m.p. 177°–179° C.

EXAMPLE 7

6-Hydroxy-7-(4-cyanophenyl)aminomethyl-3,4-dihydrobenzopyran

A mixture of 6-hydroxy-3,4-dihydrobenzopyran-7-carboxaldehyde (480 mg, 2.70 mmol) and p-aminobenzonitrile (320 mg, 2.70 mmol) in methanol (25 mL) was heated to reflux for 20 minutes. The reaction mixture was cooled to 10° C. and the intermediate Schiff's base, which had crystallized was collected by filtration (300 mg, 40%).

A portion of Schiff's base (300 mg, 1.08 mmol) was suspended in methanol (12 mL) and sodium borohydride (45 mg, 1.2 mmol) was added in portions. The mixture was stirred for 15 minutes then poured into water (75 mL). The aqueous mixture was neutralized with 2.5 N HCl (pH=7) and the product, which had precipitated, was collected by filtration and dried to afford 6-hydroxy-7-(4-cyanophenyl) aminomethyl-3,4-dihydrobenzopyran (100 mg, 30%), m.p. 162.5°–164.5° C.

EXAMPLE 8

6-Hydroxy-7-(4-carboethoxyphenyl)aminomethyl-3,4-dihydrobenzopyran

A mixture of 6-hydroxy-3,4-dihydrobenzopyran-7-carboxaldehyde (550 mg, 3.08 mmol) and p-aminoethylbenzoate (510 mg, 3.08 mmol) in methanol (25 mL) was heated to reflux for 15 minutes. The mixture was cooled to room temperature and the intermediate Schiff's base, which crystallized was collected as a yellow solid (620 mg, 62%).

A portion of Schiff's base (590 mg, 1.82 mmol) was suspended in methanol (30 mL) and sodium borohydride (80 mg, 2.1 mmol) was added in portions. Upon completion of the addition the mixture was allowed to stir at room temperature for 10 minutes then poured into water (125 mL). The aqueous mixture was neutralized (pH=7) with 2.5N HCl filtered and dried to afford 6-hydroxy-7-(4-carboethoxyphenyl) aminomethyl-3,4-dihydrobenzopyran (560 mg, 95%), m.p. 149.5–150.5° C.

EXAMPLE 9

6-Hydroxy-7-phenylaminomethyl-3,4-dihydrobenzopyran

A mixture of 6-hydroxy-3,4-dihydrobenzopyran-7-carboxaldehyde (429 mg, 2.41 mmol) and aniline (224 mg, 2.42 mmol) in methanol (30 mL) was warmed and the methanol, which distilled over, was collected. When 10 mL of methanol had been collected, the mixture was allowed to cool and the intermediate Schiff's base crystallized out. This material was collected and redissolved in fresh methanol (30 mL). Sodium borohydride (1 molar equiv.) was added in portions and the color immediately discharged. The mixture was concentrated to 50% of its original volume, then poured into an excess of water (100 mL). The aqueous solution was rendered acidic with 2N HCl, filtered to remove any insoluble material, then basified with 7%, NaHCO₃. The product, which precipitated, was collected by filtration and dried to afford 6-hydroxy-7-phenylaminomethyl-3,4-dihydrobenzopyran (277 mg, 49%), m.p. 135°–137° C.

EXAMPLE 10

6-Hydroxy-7-(2-hydroxymethylphenyl)aminomethyl-3,4-dihydrobenzopyran

A mixture of 6-hydroxy-3,4-dihydrobenzopyran-7-carboxaldehyde (400 mg, 2.27 mmol) and o-aminobenzylalcohol 282 mg, 2.25 mmol) in methanol (30 mL) was brought to a gentle boil and the volume slowly concentrated to 10 mL. An additional portion of methanol (20 mL) was added and the above process repeated two times. The mixture was cooled (ice bath) and a few drops of water added to aid in the crystallization of the Schiff's base. This material (440 mg) was collected by filtration, redissolved in methanol (30 mL) and sodium borohydride (60 mg, 1.59 mmol) was added in portions. The color was discharged immediately and the mixture allowed to stir at room temperature for 10 minutes. The reaction mixture as concentrated to half its original volume then poured into water (35 mL). After acidification (pH=5) with 2N HCl the mixture was filtered, and the filtrate basified with 7% NaHCO₃. The product, which precipitated, was collected by filtration and vacuum dried to afford 6-hydroxy-7-(2-hydroxymethylphenyl)aminomethyl-3,4-dihydrobenzopyran (300 mg, 46.8%), m.p. 141–142° C.

EXAMPLE 11

Step A: Preparation of
5-methoxy-2,3-dihydrobenzofuran-6-carboxaldehyde

A solution of 5-methoxy-2,3-dihydrobenzofuran (44.8 g, 299 mmol) in dry methylene chloride (690 mL) was cooled to 3° under nitrogen and titanium tetrachloride (53.5 mL, 92.34 g, 486 mmol) was added dropwise keeping the internal temperature below 7°. To the resulting mixture was added dropwise dichloromethylmethylether (22.3 mL, 28.34 g, 247 mmol) over one hour with the internal temperature maintained at 7°. The cooling bath was removed and the mixture allowed to stir for four hours, then quenched by the dropwise addition of water (120 mL). The resulting mixture was poured into water (100 mL) and the layers separated. The aqueous layer was washed with methylene chloride (2×250 mL), then the combined organic extracts were washed with 5% NaCl (1000 mL), dried (Na₂SO₄) and concentrated to a dark oil. Purification by preparation HPLC (Waters Prep 500, 15% ethyl acetate in hexane as eluant) afforded 5-methoxy-2,3-dihydrobenzofuran-6-carboxaldehyde as a pale yellow solid (20.64 g, 38.8%), m.p. 82–84° C.

Step B: Preparation of
5-hydroxy-2,3-dihydrobenzofuran-6-carboxaldehyde

A solution of 5-methoxy-2,3-dihydrobenzofuran-6-carboxaldehyde (24.00 g, 135 mmol) in dry methylene chloride (800 mL) under nitrogen was cooled to an internal temperature of −67°. A solution of boron tribromide (1M in methylene chloride, 63.0 mL 63.0 mmol) was added dropwise. The cooling bath was removed and the mixture allowed to stir for 2.5 hours. The reaction was then quenched by the dropwise addition of methanol (25 mL) and the resulting mixture poured into 10% aqueous sodium chloride (100 mL). The layers were separated and the aqueous layer washed with methylene chloride (2×250 mL), and the combined organic extracts washed with 10% sodium chloride (2×500 mL), dried (Na₂SO₄), and concentrated. Purification by preparative HPLC (Waters Prep 500, 9:1 hexane:ethyl acetate as eluant) afforded 5-hydroxy-2,3-dihydrobenzofuran-6-carboxaldehyde (16.82 g, 76.1%), m.p. 102–104° C.

Step C: Preparation of 5-hydroxy-6-phenylaminomethyl-2,3-dihydrobenzofuran

A mixture of 5-hydroxy-2,3-dihydrobenzofuran-6-carboxaldehyde (300 mg, 1,83 mmol) and aniline (171 mg, 1.83 mmol) in methanol (3.0 mL) was heated to reflux for 30 minutes at which point the Schiff's base had begun to crystallize. The mixture was allowed to cool and the Schiff's base collected by filtration to afford orange needles (400 mg, 91.5%).

A portion (350 mg, 1,46 mmol) of the Schiff's base was suspended in methanol (5 mL) and sodium borohydride (56.5 mg, 1.49 mmol) was added in portions over 3 minutes. The mixture was allowed to stir at room temperature for an additional ten minutes, then poured into water (40 mL). The resulting white suspension was acidified with 2N HCl, filtered, and the filtrate basified with 7% aqueous NaHCO₃. The product, which precipitated, was collected by filtration and vacuum dried to afford 5-hydroxy-6-phenylaminomethyl-2,3-dihydrobenzofuran (305 mg, 86.4%), m.p. 130–131° C.

EXAMPLE 12

5-Hydroxy-6-(2-hydroxymethylphenyl)aminomethyl-2,3-dihydrobenzofuran

A mixture of 5-hydroxy-2,3-dihydrobenzofuran-6-carboxaldehyde (300 mg, 1.83 mmol) and o-aminobenzylalcohol (230 mg, 1.83 mmol) in methanol (5.0 mL) was heated to reflux for thirty minutes. The mixture was cooled gradually to room temperature and after some time the Schiff's base crystallized. After filtration and drying a yellow orange product (290 mg, 59%) was obtained.

A portion (250 mg. 0.93 mmol) of the Schiff's base was suspended in methanol (5 mL) and sodium borohydride (35 mg, 0.93 mmol) was added in portions. The color was discharged and the reaction mixture allowed to stir at room temperature for ten minutes, then poured into water (35 mL). The resulting suspension was rendered slightly acidic with 2N HCl, filtered, and the filtrate basified with 7% NaHCO₃. The product, which precipitated, was filtered and vacuum dried to afford 5-hydroxy-6-(2-hydroxymethylphenyl)aminomethyl-2,3-dihydrobenzofuran (226 mg, 89.7%), m.p. 149–150° C.

EXAMPLE 13

5-Hydroxy-6-(2,4-difluorophenyl)aminomethyl-2,3-dihydrobenzofuran

A mixture of 5-hydroxy-2,3-dihydrobenzofuran-6-carboxaldehyde (305 mg, 1.86 mmol) and 2,4-difluoroaniline (242 mg, 1.86 mmol) was heated to reflux. After a few minutes a voluminous precipitate formed and an additional portion of methanol (2 mL) was added. Heating was continued for an additional 10 minutes, then the mixture was allowed to cool and the intermediate Schiff's base collected by filtration (400 mg, 785).

The Schiff's base was suspended in methanol (20 mL) and sodium borohydride (55 mg, 1.45 mmol) was added in portions. After a few minutes a clear solution was obtained and the mixture poured into water (100 mL). The product, which precipitated, was collected by filtration and vacuum dried to afford 5-hydroxy-6-(2,4-difluorophenyl)aminomethyl-2,3-dihydrobenzofuran (335 mg, 83%), m.p. 119–121° C.

EXAMPLE 14

5-Hydroxy-6-(4-acetylphenyl)aminomethyl-2,3-dihydrobenzofuran

A mixture of 5-hydroxy-2,3-dihydrobenzofuran-6-carboxaldehyde (317 mg, 1.93 mmol) and p-aminoacetophenone (261 mg, 1.93 mmol) in methanol (10 mL) was heated to reflux for 90 minutes. The resulting mixture was allowed to cool and the intermediate Schiff's base collected by filtration (490 mg, 90%).

A portion of Schiff's base (445 mg, 1.58 mmol) in methanol (20 mL) was hydrogenated at 40 psi over 10% palladium on carbon (50 mg). After the appropriate amount of hydrogen had been absorbed, the reaction mixture was warmed to dissolve some suspended solid then filtered through Celite. The filtrate was concentrated to a total volume of 5 mL and the product, which had crystallized, was collected by filtration and dried to afford 5-hydroxy-6-(4-acetylphenyl)aminomethyl-2,3-dihydrobenzofuran (250 mg, 56%), m.p. 181–183° C.

EXAMPLE 15

6-[2-cyanothien-4(and 5)-yl]aminomethyl-5-hydroxy-2,3-dihydrobenzofuran

Step A: Preparation of 2-cyano-4(and 5)-nitrothiophene

In a 500 ml round bottom flask, a mixture of 150 ml glacial acetic acid and 30 ml fuming nitric acid (90%) was stirred at 10° C. To this mixture 2-cyanothiophene (11.2 g, 0.103 mole) in 25 ml acetic anhydride were added slowly over a period of 45 minutes while maintaining the temperature below 25° C. The resulting solution was stirred at ambient temperature for 16 hours before it was poured into 300 ml of ice water and extracted with 700 ml of ether. The organic layer was separated dried over anhydrous MgSO₄ and concentrated in vacuo. The resulting crude product was crystallized from ether/hexane (1:2) to yield a yellow solid which was shown by NMR to be a 3 to 1 mixture of 2-cyano-4-nitrothiophene and 2-cyano-5-nitrothiophene.

Step B: Preparation of 2-cyano-4(and 5)-aminothiophene

To a stirring solution of 4-nitro and 5-nitro-2cyanothiophene (3:1 mixture, 4.62 g, 30 mmol) in 100 ml of ethyl acetate was added 5.0 g of 10% Pd/c under 50 psi of hydrogen. The theoretical amount of hydrogen was consumed in 2 hours and the reaction mixture was filtered through a celite filter aid. The product, a mixture of 2-cyano-4-aminothiophene and 2-cyano-5-aminothiophene in ethyl acetate was used directly in the next reaction without further purification.

Step C: Preparation of 6-[2-cyanothiene-4(and 5)-yl]iminomethyl-5-hydroxy-2,3-dihydrobenzofuran Five mililiters of the mixture was transferred under nitrogen atmosphere to a 25 ml round bottom flask containing 200 mg of 5-hydroxy-2,3-dihydrobenzofuran-6-carboxyladehyde and 1 mg of p-toluene sulfonic acid. The mixture was stirred at ambient temperature for 40 minutes. The resulting orange solid was filtered and air dried to yield 250 mg (70% yield) of a crude mixture of 6-[2-cyanothien-4(and 5)-yl]iminimethyl-5-hydroxy-2,3-dihydrobenzofuran.

Step D: Preparation of 6-[2-cyanothiene-4(and 5)-yl]aminomethyl-5-hydroxy-2,3,dihydrobenzofuran To a suspension of 250 mg of the crude product from Step C in 5 ml of absolute ethanol was added 50 mg of sodium borohydride stirred at room temperature for one hour. It was concentrated in vacuo extracted with ethyl acetate (2×10 ml), dried, and by flash column chromatography (silica 3:1 hexane:ethyl acetate) was separated into the two isomeric products. The front running fraction gave 6-(2-cyanothiene-4-yl)aminomethyl-5-hydroxy-2,3-dihydrobenzofuran (130 mg, m.p. 138–139° C.); and the slower fraction afforded 6-(2-cyanothien-5-yl)aminomethyl-5-hydroxy-2,3-dihydrobenzofuran (55 mg, m.p. 158–160° C.).

EXAMPLE 16

7-[2-cyanothien-4(and 5)-yl]aminomethyl-6-hydroxy-3,4-dihydrobenzopyran

Following substantially the same procedures as described in Example 15, but substituting for the 5-hydroxy-2,3-dihydrobenzofuran-6-carboxyaldehyde used therein 6-hydroxy-3,4-dihydrobenzopyran-7-carboxyaldehyde, there were prepared the following compounds:

(a) 7-(2-cyanothien-4-yl)aminomethyl-6-hydroxy-3,4-dihydrobenzopyran, m.p. 149°–153° C.; and (b) 7-(2-cyanothien-5-yl)aminomethyl-6-hydroxy-3,4-dihydrobenzofuran, m.p. 139°–139.5° C.

What is claimed is:

1. A compound of formula (I)

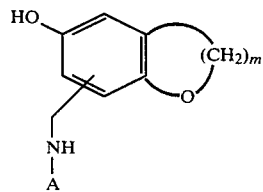

(I)

or a pharmaceutically acceptable salt thereof wherein m is an integer selected from 2 or 3;

A is (a) phenyl or phenyl substituted with ($R^1$) wherein when there are more than one $R^1$ (q>1) $R^1$ can be the same or different from each other and is
(1) halo;
(2) loweralkoxy;
(3) lower alkylthio;
(4) lower alkyl sulfinyl;
(5) lower alkyl sulfonyl;
(6) phenyl or phenyl substituted with a functional group selected from a group consisting of halo, $C_{1-6}$alkyl, $C_{1-6}$haloalkyl, $C_{1-6}$alkoxy, $C_{1-6}$alkanoyl, $C_{1-6}$alkylthio, $C_{1-6}$alkylsulfinyl, $C_{1-6}$alkylsulfonyl, —COOH or COOC$_{1-6}$alkyl, cyano, hydroxyC$_{1-6}$alkyl, halo$_{1-6}$alkanoyl and lower alkanoyloxy;
(7) loweralkyl;
(8) loweralkenyl;
(9) lower alkanoyl;
(10) haloloweralkyl;
(11) —COOH or —COOC$_{1-6}$alkyl;
(12) cyano;
(13) hydroxyloweralkyl;
(14) halo loweralkanoyl; or
(15) loweralkanoyloxy;

q is an integer ranging from 1 to 5;

(b) unsubstituted or substituted heteroaryl selected from a group consisting of:
(1) thienyl;
(2) benzothienyl;
(3) furyl;
(4) benzofuryl;
(5) pyrryl;
(6) indolyl;
(7) thiazolyl;
(8) benzothiazolyl;
(9) thiadiazolyl;
(10) benzothiadiazolyl;
(11) quinolyl;
(12) isoquinolyl;
(13) pyrazinyl;
(14) tetrazolyl; or
(15) triazolyl, the heteroaryl above being substituted with one or more of $R^1$ with the proviso that when m is 2, the ANH group cannot be at the position ortho to the O of the oxa ring.

2. The compound of formula (I) according to claim 1 wherein:

A is phenyl or phenyl substituted with ($R^1$) wherein $R^1$ is
(a) loweralkoxy;
(b) halo;
(c) lowerhaloalkyl,
(d) loweralkanoyl;
(e) hydroxyloweralkyl; or
(f) CN;

q is 1 or 2; and m is 2 or 3.

3. The compound of claim 1 having formulae:

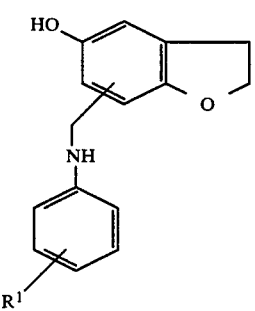

(a)

and

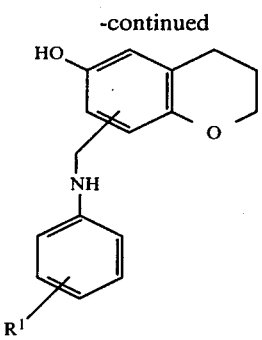

(b)

wherein R¹ is loweralkanoyl or hydroxyloweralkyl.

4. The compound of claim 1 which is
(a) 2,3-dihydro-5-hydroxy-6-(2-hydroxymethylphenylaminomethyl)benzofuran;
(b) 6-(4-acetylphenylaminomethyl)-2,3-dihydro-5-hydroxybenzofuran;
(c) 6-hydroxy-7-(4-acetylphenyl)aminomethyl-3,4-dihydrobenzopyran;
(d) 6-hydroxy-5-(4-acetylphenyl)aminomethyl-3,4-dihydrobenzopyran;
(e) 6-hydroxy-7-(2-hydroxymethylphenyl)aminomethyl-3,4-dihydrobenzopyran; or
(f) 6-hydroxy-5-(2-hydroxymethylphenyl)aminomethyl-3,4-dihydrobenzopyran.

5. A pharmaceutical composition for treating topical inflammation comprising a pharmaceutical carrier and an effective amount of a compound of formula (I)

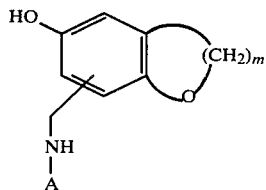

(I)

or a pharmaceutically acceptable salt thereof wherein
m is an integer selected from 2 or 3;
A is
(a) phenyl or phenyl substituted with $(R^1)_q$ wherein when there are more than one $R^1$ (q>1) $R^1$ can be the same or different from each other and is
(1) halo;
(2) loweralkoxy;
(3) lower alkylthio;
(4) lower alkyl sulfinyl;
(5) lower alkyl sulfonyl;
(6) phenyl or phenyl substituted with a functional group selected from a group consisting of halo, $C_{1-6}$alkyl, $C_{1-6}$haloalkyl, $C_{1-6}$alkoxy, $C_{1-6}$alkanoyl, $C_{1-6}$alkylthio, $C_{1-6}$alkylsulfinyl, $C_{1-6}$alkylsulfonyl, —COOH or COOC$_{1-6}$alkyl, cyano, hydroxyC$_{1-6}$alkyl, halo$_{1-6}$alkanoyl and lower alkanoyloxy;
(7) loweralkyl;
(8) loweralkenyl;
(9) lower alkanoyl;
(10) haloloweralkyl;
(11) —COOH or —COOC$_{1-6}$alkyl;
(12) cyano;
(13) hydroxyloweralkyl;
(14) halo loweralkanoyl;
or
(15) loweralkanoyloxy;
q is an integer ranging from 1 to 5;
(b) unsubstituted or substituted heteroaryl selected from a group consisting of:
(1) thienyl;
(2) benzothienyl;
(3) furyl;
(4) benzofuryl;
(5) pyrryl;
(6) indolyl;
(7) thiazolyl;
(8) benzothiazolyl;
(9) thiadiazolyl;
(10) benzothiadiazolyl;
(11) quinolyl;
(12) isoquinolyl;
(13) pyrazinyl;
(14) tetrazolyl; or
(15) triazolyl,
the heteroaryl above being substituted with one or more of R¹ with the proviso that when m is 2, the ANH group cannot be at the position ortho to the O of the oxa ring.

6. The pharmaceutical composition of claim 5 wherein:
A is phenyl or phenyl substituted with $(R^1)_q$ wherein R¹ is
(a) loweralkoxy;
(b) halo;
(c) lowerhaloalkyl,
(d) loweralkanoyl;
(e) hydroxyloweralkyl; or
(f) CN;
q is 1 or 2; and
m is 2 or 3.

7. The pharmaceutical composition of claim 5 wherein the active compound is of formula:

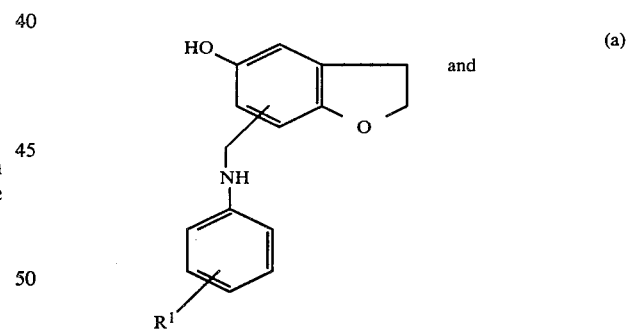

(a)

and

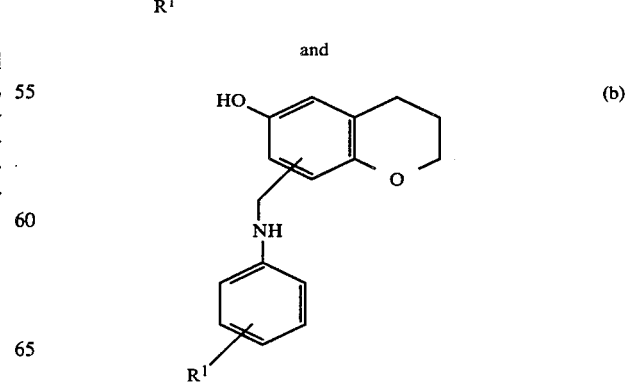

(b)

wherein R¹ is loweralkanoyl or hydroxyloweralkyl.

8. The pharmaceutical composition of claim 6 wherein the active compound is
(a) 2,3-dihydro-5-hydroxy-6-(2-hydroxymethylphenylaminomethyl)benzofuran;
(b) 6-(4-acetylphenylaminomethyl)-2,3-dihydro-5-hydroxybenzofuran;
(c) 6-hydroxy-7-(4-acetylphenyl)aminomethyl-3,4-dihydrobenzopyran;
(d) 6-hydroxy-5-(4-acetylphenyl)aminomethyl-3,4-dihydrobenzopyran;
(e) 6-hydroxy-7-(2-hydroxymethylphenyl)aminomethyl-3,4-dihydrobenzopyran; or
(f) 6-hydroxy-5-(2-hydroxymethylphenyl)aminomethyl-3,4-dihydrobenzopyran.

9. A method of treating or decreasing topical inflammation comprising the administration to a mammalian species in need of such treatment a therapeutically effective amount of a compound of formula I

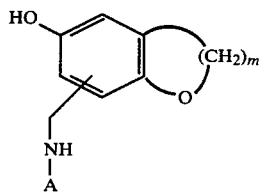
(I)

or a pharmaceutically acceptable salt thereof wherein
m is an integer selected from 2 or 3;
A is
(a) phenyl or phenyl substituted with $(R^1)_q$ wherein when there are more than one $R^1$ (q>1) $R^1$ can be the same or different from each other and is
(1) halo;
(2) loweralkoxy;
(3) lower alkylthio;
(4) lower alkyl sulfinyl;
(5) lower alkyl sulfonyl;
(6) phenyl or phenyl substituted with a functional group selected from a group consisting of halo, $C_{1-6}$alkyl, $C_{1-6}$haloalkyl, $C_{1-6}$alkoxy, $C_{1-6}$alkanoyl, $C_{1-6}$alkylthio, $C_{1-6}$alkylsulfinyl, $C_{1-6}$alkylsulfonyl, —COOH or COOC$_{1-6}$alkyl, cyano, hydroxyC$_{1-6}$alkyl, halo$_{1-6}$alkanoyl and lower alkanoyloxy;
(7) loweralkyl;
(8) loweralkenyl;
(9) lower alkanoyl;
(10) haloloweralkyl;
(11) —COOH or —COOC$_{1-6}$alkyl;
(12) cyano;
(13) hydroxyloweralkyl;
(14) halo loweralkanoyl;
(15) loweralkanoyloxy;
q is an integer ranging from 1 to 5;
(b) unsubstituted or substituted heteroaryl selected from a group consisting of:
(1) thienyl;
(2) benzothienyl;
(3) furyl;
(4) benzofuryl;
(5) pyrryl;
(6) indolyl;
(7) thiazolyl;
(8) benzothiazolyl;
(9) thiadiazolyl;
(10) benzothiadiazolyl;
(11) quinolyl;
(12) isoquinolyl;
(13) pyrazinyl;
(14) tetrazolyl; or
(15) triazolyl,
the heteroaryl above being substituted with one or more of $R^1$ with the proviso that when m is 2, the ANH group cannot be at the position ortho to the O of the oxa ring.

10. The method of claim 9 wherein:
A is phenyl or phenyl substituted with $(R^1)_q$ wherein $R^1$ is
(a) loweralkoxy;
(b) halo;
(c) lowerhaloalkyl,
(d) loweralkanoyl;
(e) hydroxyloweralkyl; or
(f) CN;
q is 1 or 2; and
m is 2 or 3.

11. The method of claim 9 wherein the active compound is of formula:

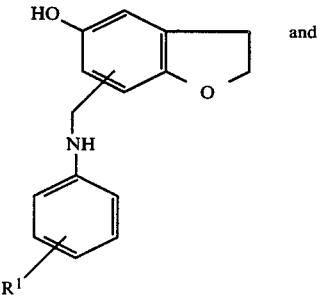
(a)

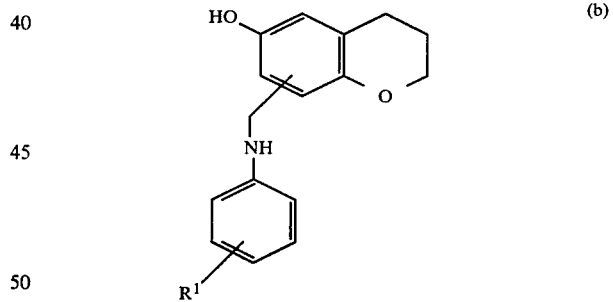
(b)

wherein $R^1$ is loweralkanoyl or hydroxyloweralkyl.

12. The method of claim 9 wherein the active compound is:
(a) 2,3-dihydro-5-hydroxy-6-(2-hydroxymethylphenylaminomethyl)benzofuran;
(b) 6-(4-acetylphenylaminomethyl)-2,3-dihydro-5-hydroxybenzofuran;
(c) 6-hydroxy-7-(4-acetylphenyl)aminomethyl-3,4-dihydrobenzopyran;
(d) 6-hydroxy-5-(4-acetylphenyl)aminomethyl-3,4-dihydrobenzopyran;
(e) 6-hydroxy-7-(2-hydroxymethylphenyl)aminomethyl-3,4-dihydrobenzopyran; or
(f) 6-hydroxy-5-(2-hydroxymethylphenyl)aminomethyl-3,4-dihydrobenzopyran.

* * * * *